May 26, 1959 H. C. SWIM ET AL Plant Pat. 1,837
ROSE PLANT
Filed Nov. 3, 1958
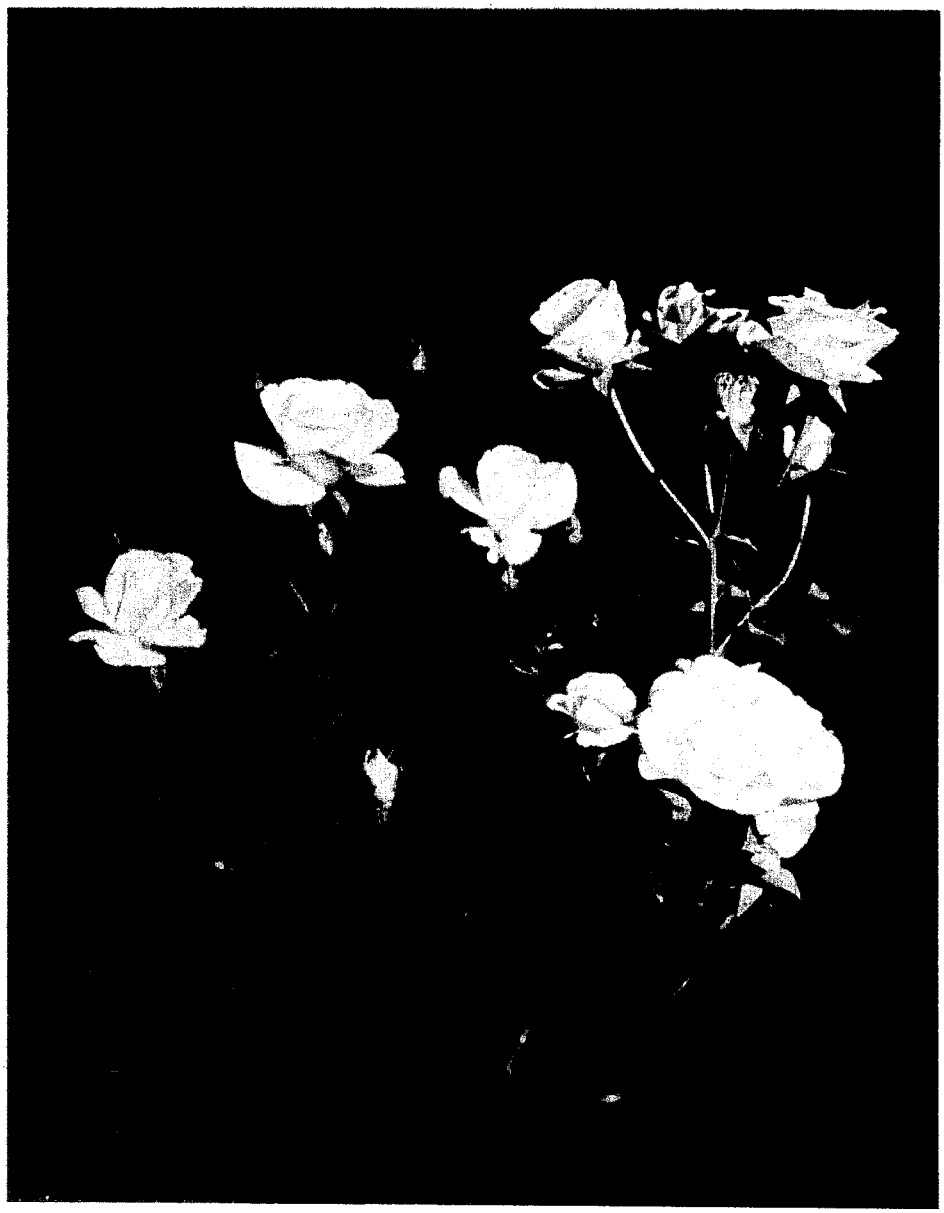
INVENTORS
H. C. Swim and
O. L. Weeks
BY Robb & Robb
ATTORNEYS United States Patent Office Plant Pat. 1,837
Patented May 26, 1959

1,837

ROSE PLANT

Herbert C. Swim, Ontario, and O. L. Weeks, Chino, Calif.

Application November 3, 1958, Serial No. 771,687

1 Claim. (Cl. 47—61)

The present invention relates to a new and distinct variety of rose plant of the hybrid polyantha class, which was originated by us by crossing the variety "Pinocchio" (Plant Patent No. 484) with the unpatented variety "Virgo."

The primary objective sought to be achieved by this breeding was to produce a new rose variety which combines the most desirable traits of the parents, particularly in respect to the attainment of good flower productivity that would be suitable for use as a greenhouse rose for producing cut flowers for the florist trade. This objective was fully achieved, along with other desirable improvements, as evidenced by the following unique combination of characteristics which are outstanding in the new variety and distinguish it from its parents, as well as from all other varieties of which we are aware:

(1) High flower productivity, with many of the flowers borne on individual stems, although in some instances with relatively fewer flowers per stem than is usual in roses of this class;

(2) Strong, straight stems which grow mainly in an upright position;

(3) An ability of the stems to take up water after they are cut and placed in water, so that the tight buds continue to develop and grow to maturity in a normal manner, thus giving the flowers the long-lasting quality so desirable in a florist rose;

(4) A long pointed shape of the flower buds, with each bud composed of petals slightly broader than their length;

(5) A flower which holds the form of the bud in its center until the flower has completely opened, and being pointed to a large extent, but which occasionally may have the center petals folded over one another with a globular effect to the center in hot weather; and (6) A relatively high degree of purity of the white color of the buds and flowers, as compared with other known rose varieties.

In comparison with its seed parent, "Pinocchio," our new variety is more upright in its habit of growth; produces its flowers in smaller clusters, with fewer flowers per cluster; the buds are larger and more slender in their proportions, and the open flowers are also larger; the flowers rarely have more than 19 petals, whereas those of "Pinocchio" rarely have less than 30; and the flowers are white, whereas those of "Pinocchio" may be generally described as salmon pink in color.

As compared with its pollen parent, "Virgo," the new variety is a typical floribunda, with medium sized flowers (ranging from about 2½ inches to about 3 inches in diameter), in comparison with the flowers of other varieties of this class, whereas the flowers of this parent are of the hybrid tea type and attain a diameter of 4 inches or more; and our new variety is more resistant to mildew than this parent when grown under comparable cultural conditions.

Asexual reproduction of our new variety by budding, as performed at Chino, California, shows that the aforementioned characteristics and distinctions come true to form and are established and transmitted through succeeding propagations.

The accompanying drawing shows typical specimens of the vegetative growth and flowers of our new variety in different stages of development and as depicted in color as nearly true as it is reasonably possible to make the same in a color illustration of this character.

The following is a detailed description of our new variety, with color terminology in accordance with the Nickerson Color Fan, published by Munsell Color Company Incorporated, of Baltimore, Maryland, except where general color terms of ordinary dictionary significance are obvious:

Type: bush; greenhouse; seedling; for cut flowers.
Class: Hybrid polyantha.
Breeding: Seedling.
*Seed parent.*—"Pinocchio."
*Pollen parent.*—"Virgo."
Propagation: Holds its distinguishing characteristics through succeeding propagations by budding.

*Flower*

Locality where grown and observed: Chino, California.
Flowers borne: Usually singly, but sometimes from 2 to 5 per stem; in irregular clusters; on long stems of normal strength.
Quantity of bloom: Abundant, in greenhouse.
Continuity: From intermittent to continuous.
Fragrance: Moderate. Nature—musk-tea combination.
Bud:
*Peduncle.*—Long; medium caliper; erect; stiff; almost smooth; with few glands. Color—medium green.
*Before calyx breaks.*—Size—Medium. Form—short; pointed; ovoid; without foliaceous appendanges on the surface of the bud; with almost entire parts extending beyond the tip of the bud equal to ¼ of its length. Color—between Strong Yellow Green, 7.5GY6/8 and Moderate Yellow Green, 7.5GY5/7.
*As calyx breaks.*—Color—between Light Yellow Green, 7.5GY9/4 and white.
*As first petal opens.*—Size—medium for this type. Form—long; pointed. Color: outside—between Light Yellow Green, 7.5GY9/4 and Brilliant Yellow Green, 2.5GY9/8 at base, progressing to white at apex; inside—near Light Yellow Green, 7.5GY9/4 at base, with remainder white.
*Opening.*—Opens up well.
Bloom:
*Size (when fully open).*—Medium for this type; from 2½ inches to 3 inches.
*Petalage.*—Semi-double; from 14 to 19 petals, plus from 1 to 3 petaloids; arranged regularly.
*Form.*—High-centered at first, but becoming from flat to cupped; petals at first being very slightly rolled outward, but later becoming from flat to slightly cupped in center of flower at maturity.
Petals:
*Texture.*—Thick; leathery. Inside—crepe-like. Outside—shiny-satiny.
*Shape.*—Outside—oval. Intermediate—oval. Inside—round, with apex occasionally having 1 notch.

This description of a newly opened flower was made from a rose grown outdoors in the month of September at Chino, California:

*Color.*—Outer petal: outside surface—white, shaded at base Brilliant Yellow Green, 2.5GY9/8; inside surface—white, shaded toward base Brilliant Yellow Green, 2.5GY9/8. Intermediate petal: outside surface—white, shaded at base Brilliant Yellow Green, 2.5GY9/8; inside surface—white, shaded toward base Brilliant Yellow Green, 2.5GY9/8. Inner petal: outside surface—white, shaded toward base Brilliant Yellow Green, 2.5GY9/8; inside surface—white, shaded toward base Brilliant Yellow Green, 2.5GY9/8.

This description was made from a rose that was grown outdoors but cut and allowed to remain open for 3 days indoors in the month of September at Chino, California:

*Color.*—Outer petal: outside surface—white, shaded at base Brilliant Yellow Green, 2.5GY9/8; inside surface—white, shaded at base Brilliant Yellow Green, 2.5GY9/8. Inner petal: outside surface—white, shaded at base Brilliant Yellow Green, 2.5GY9/8; inside surface—white, shaded at base Brilliant Yellow Green, 2.5GY9/8.

*General color effect.*—Newly opened flower—white, shaded at base Brilliant Yellow Green, 2.5GY9/8. 3-days open—white, shaded at base Brilliant Yellow Green, 2.5GY9/8.

*Behavior.*—Drop off cleanly; a few petals and petaloids persist and turn brown as the result of hot, dry weather.

*Flower longevity.*—On bush in garden—5 days in September. Cut roses grown outdoors and kept at living-room temperatures—4 days in September.

*Reproductive organs*

Stamens: Most arranged irregularly, partly about pistils; some intertwined with pistils; usually about 200 plus in number. Color—between Pale Orange Yellow, 7.5YR9/4 and Moderate Orange Yellow, 7.5YR8/8.

Filaments: Medium length; most with anthers. Color—yellow.

Anthers: Small; most open at once. Color—between Pale Orange Yellow, 7.5YR9/4 and Moderate Orange Yellow, 7.5YR8/8.

Pollen: Moderate. Color—yellow.

Pistils: From medium number to many.

Styles: Very uneven; from short to medium length; medium heavy; bunched. Color—reddish near stigma.

Stigma: Color—light silvery gray.

Ovaries: Most enclosed in calyx, but some protruding therefrom.

Hips: Globular; smooth; walls fleshy and of medium thickness. Color—from orange yellow to russet.

Sepals: Permanent; moderately short; from spear shaped to recurved. Color—near Moderate Yellow Green, 5GY5/6.

Seeds: From few to many; usually from 8 to 10 in number.

*Plant*

Foliage:

*Leaves.*—Compound of 3, 5 or 7 leaflets; normal abundance; medium large; moderately heavy; leathery.

*Leaflets.*—Shape—ovoid, with apex acute. Base—round. Margin—from simply to doubly serrate.

*Color.*—Mature: upper surface—dark green; under surface—gray-green. Young: upper surface—green, with reddish margin; under surface—gray-green, with red overlay.

*Rachis (the supporting stem of the compound leaf).*—Medium caliper. Upper side—grooved; many glands. Under side—moderately prickly and glandular.

*Stipules.*—Moderately short; narrow; with short points turning out at an angle of more than 45°.

*Disease resistance.*—Good resistance to mildew, as compared with average greenhouse roses grown in greenhouse under comparable cultural conditions at Chino, California.

Growth:

*Habit.*—Bushy; upright; much-branched.

*Growth.*—Vigorous.

*Canes.*—Medium caliper.

*Main stems.*—Color—bright green. Large prickles—several; medium length; straight, with short, broad base. Small prickles—few; color—brown. Hairs—none.

*Branches.*—Color—bright yellow green. Large prickles—several; medium length; straight; with short, broad base. Small prickles—few; color—brown. Hairs—none.

*New shoots.*—Color—gray-green. Large prickles—several; medium length; straight; with short, broad base. Small prickles—few; color—light green, shading to reddish at base. Hairs—none.

We claim:

A new and distinct variety of rose plant of the hybrid polyantha class, substantially as herein shown and described, characterized particularly as to novelty by the unique combination of high flower productivity, with the flowers borne sometimes individually and sometimes with relatively few flowers per stem, said stems being straight and strong and usually having an ability of the stems to take up water after being cut and disposed in water, with consequent development and growth of tight buds to maturity in a normal manner and with attendant long-lasting flower qualities suitable for a florist rose, said flower buds being of long pointed shape and composed of petals slightly broader than their length, a flower habit of holding the form of the bud in the center of each flower until the flower has completely opened, with consequent pointed form of the flowers to a large extent, but with occasional flowers having their center petals folded over one another and giving a globular effect to the center in hot weather, and a relatively pure white general color tonality of the buds and flowers.

No references cited.